(12) United States Patent
Ishida (10) Patent No.: US 8,896,681 B2
(45) Date of Patent: Nov. 25, 2014

(54) IMAGE PICKUP UNIT FOR ENDOSCOPE

(71) Applicant: Olympus Medical Systems Corp., Tokyo (JP)

(72) Inventor: Yuya Ishida, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/948,705

(22) Filed: Jul. 23, 2013

(65) Prior Publication Data

US 2014/0009592 A1 Jan. 9, 2014

Related U.S. Application Data

(63) Continuation of application No. PCT/JP2012/072925, filed on Sep. 7, 2012.

(30) Foreign Application Priority Data

Mar. 6, 2012 (JP) ................. 2012-049463

(51) Int. Cl.
| | |
|---|---|
| *H04N 5/225* | (2006.01) |
| *A61B 1/00* | (2006.01) |
| *G02B 7/02* | (2006.01) |
| *G02B 7/04* | (2006.01) |
| *G02B 23/24* | (2006.01) |
| *H04N 7/18* | (2006.01) |

(52) U.S. Cl.
CPC ........... *H04N 5/2253* (2013.01); *H04N 5/2254* (2013.01); *A61B 1/00188* (2013.01); *G02B 7/025* (2013.01); *G02B 7/04* (2013.01); *G02B 23/2423* (2013.01); *G02B 23/2469* (2013.01); *A61B 1/0011* (2013.01); *H04N 7/183* (2013.01)

USPC ............................................................. 348/76

(58) Field of Classification Search
CPC .................................................... H04N 5/2254
USPC ............................................................. 348/76
See application file for complete search history.

(56) References Cited

U.S. PATENT DOCUMENTS

2009/0076332 A1  3/2009  Iwasaki et al.

FOREIGN PATENT DOCUMENTS

| EP | 2 039 931 A2 | 3/2009 |
|---|---|---|
| JP | 63-002016 A | 1/1998 |
| JP | 2007-229155 A | 9/2007 |
| JP | 2009-085031 A | 4/2009 |
| JP | 2010-220797 A | 10/2010 |
| JP | 2011-224277 A | 11/2011 |

*Primary Examiner* — Dave Czekaj
*Assistant Examiner* — Jonathan Messmore
(74) *Attorney, Agent, or Firm* — Scully, Scott, Murphy & Presser, P.C.

(57) ABSTRACT

According to this invention, there is provided an image pickup unit for an endoscope, including a lens barrel portion includes a movable lens holding barrel that holds the movable lens and is movable to advance and retract and a drive mechanism portion which is disposed at a side surface portion of the lens barrel portion and drives the movable lens holding barrel. The unit has a holding portion which is disposed at the side surface portion of the lens barrel portion and is configured to position and hold the drive mechanism portion, a gap between the lens barrel portion and the drive mechanism portion is filled with an adhesive which is made to have a difference in hardness such that hardness is lower on a proximal end side than on a distal end side.

3 Claims, 7 Drawing Sheets

IMAGE PICKUP UNIT FOR ENDOSCOPE

CROSS REFERENCE TO RELATED APPLICATION

This application is a continuation application of PCT/JP2012/072925 filed on Sep. 7, 2012 and claims benefit of Japanese Application No. 2012-049463 filed in Japan on Mar. 6, 2012, the entire contents of which are incorporated herein by this reference.

BACKGROUND OF THE INVENTION

1. Field of the Invention

The present invention relates to an image pickup unit for an endoscope having a movable lens drive section which is disposed at a distal end portion of an endoscope insertion portion and moves some or all of objective lenses.

2. Description of the Related Art

Endoscopes which can be introduced from outside of a living body or a structure into an inside and include an image pickup unit for picking up an optical image are utilized in, e.g., fields of medicine and industry in order to observe a spot difficult to observe, such as an inside of a living body or an inside of a structure.

An image pickup unit of an endoscope includes an objective lens which forms an object image and an image pickup device (typically, a CCD (charge coupled device) or a CMOS (complementary metal oxide semiconductor) sensor) which is disposed at an image formation surface of the objective lens.

For example, Japanese Patent Application Laid-Open Publication No. 2007-229155 discloses an image pickup unit for an endoscope which has a movable lens among objective lenses and is provided with a function of changing a photographing magnification by moving the movable lens in an optical axis direction (a variable-power function or a zoom function).

In a technique disclosed in Japanese Patent Application Laid-Open Publication No. 2007-229155, the image pickup unit for an endoscope is configured to include a lens barrel portion including a movable lens holding barrel which holds the movable lens and is capable of moving to advance and retract in the optical axis direction and an image pickup device and a drive mechanism portion which is disposed at a side portion of the lens barrel portion. An arm portion protruding outwardly in a radial direction is provided at the movable lens holding barrel. The drive mechanism portion is configured to drive the movable lens holding barrel in the optical axis direction by pushing and pulling the arm portion. The lens barrel portion and the drive mechanism portion of the image pickup unit for an endoscope are shaped to extend in a direction toward a proximal end separately from each other.

SUMMARY OF THE INVENTION

An image pickup unit for an endoscope according to one aspect of the present invention is an image pickup unit for an endoscope, including a lens barrel portion which is configured to hold an objective lens including a movable lens disposed on a distal end side and an image pickup device disposed closer to a proximal end side than the objective lens and includes a movable lens holding barrel that holds the movable lens and is movable to advance and retract and a drive mechanism portion which is disposed at a side surface portion of the lens barrel portion and drives the movable lens holding barrel, wherein the unit has a holding portion which is disposed at the side surface portion of the lens barrel portion and is configured to position and hold the drive mechanism portion, the drive mechanism portion is shaped to extend in a direction toward a proximal end with a gap with the lens barrel portion on a side closer to the proximal end than the holding portion, and the gap between the lens barrel portion and the drive mechanism portion is filled with an adhesive which is made to have a difference in hardness such that hardness is lower on a proximal end side than on a distal end side.

DETAILED DESCRIPTION OF THE PREFERRED EMBODIMENT

A preferred embodiment of the present invention will be described below with reference to the drawings. Note that each constituent element is differently scaled in the individual drawings used in a following description such that the constituent element has a recognizable size on the drawings and that the present invention is not limited only to the quantity of constituent elements, shapes of constituent elements, size ratios among constituent elements, and relative positional relationships among individual constituent elements described in the drawings.

An example of an embodiment of the present invention will be described below. An example of a configuration of an endoscope 101 including an image pickup unit 1 for an endoscope according to the present invention will first be described with reference to FIG. 1. Note that the image pickup unit 1 for an endoscope will be simply referred to as the image pickup unit 1 hereinafter. The endoscope 101 according to the present embodiment can be introduced into a subject, such as a human body, and is configured to optically pick up an image of a predetermined site to be observed inside a subject. Note that a subject into which the endoscope 101 is to be introduced is not limited to a human body and may be another living body or an artifact, such as a machine or a building structure.

Figure 1:
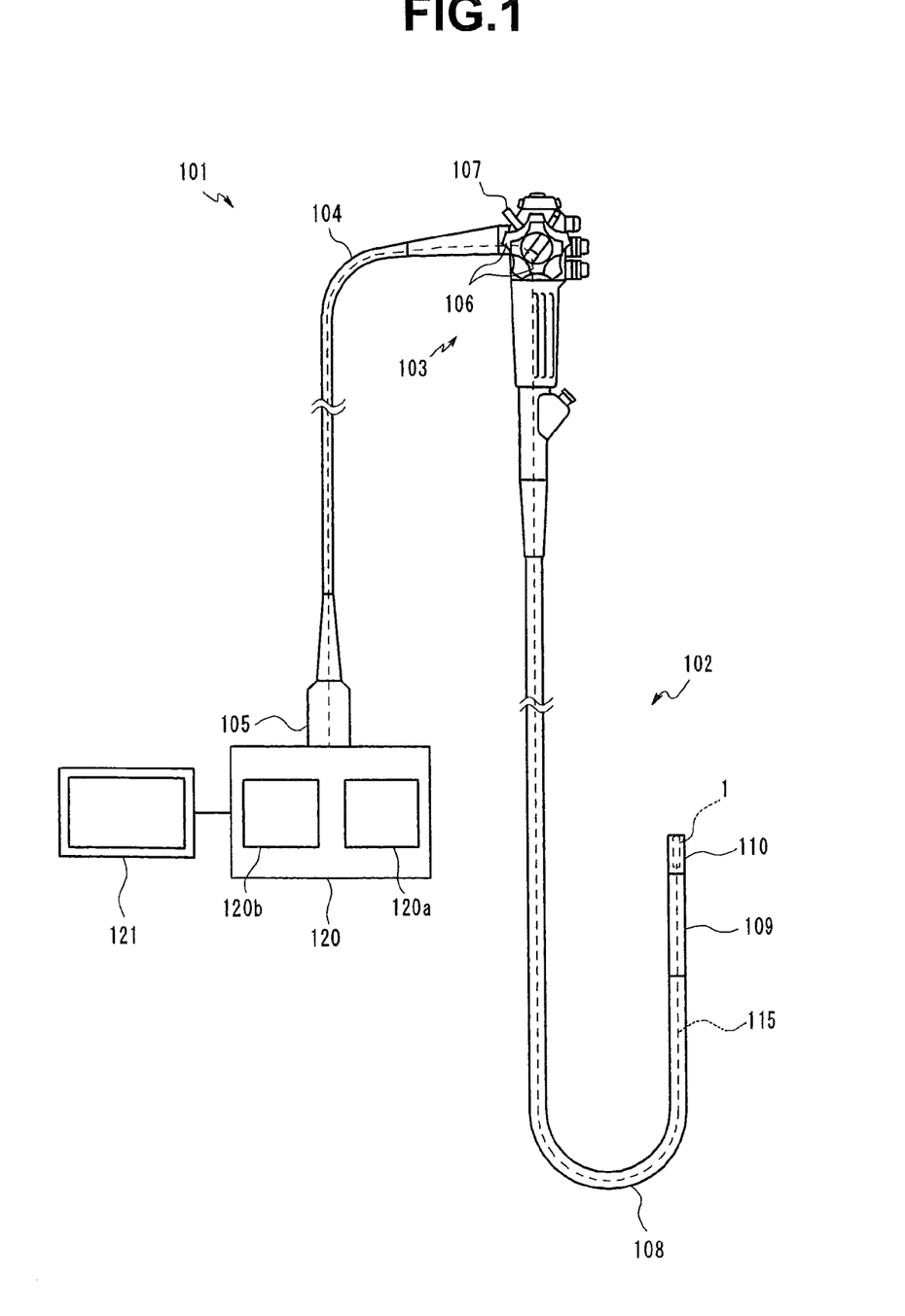
FIG. 1 is a view for explaining an endoscope including an image pickup unit for an endoscope.

The endoscope 101 is mainly composed of an insertion portion 102 which is to be introduced into an inside of a subject, an operation portion 103 which is located at a proximal end of the insertion portion 102, and a universal cord 104 which extends from a side portion of the operation portion 103.

The insertion portion 102 is composed of a distal end portion 110 disposed at a distal end, a bendable bending portion 109 disposed closer to a proximal end side than the distal end portion 110, and a flexible tube portion 108 with flexibility disposed closer to the proximal end side than the bending portion 109 and connected to a distal end side of the operation portion 103, which are provided so as to be continuous. Note that the endoscope 101 may be in a form of a so-called rigid endoscope not including a part with flexibility at an insertion portion.

As will be described in detail later, the image pickup unit 1 and an illuminating light emitting portion 113 (not shown in FIG. 1) are provided at the distal end portion 110. An angle operation knob 106 for operating the bending portion 109 such that the bending portion 109 is bent is provided at the operation portion 103. A variable-power operation portion 107 which is a lever switch for ordering action of a drive mechanism portion 30 (to be described later) and performing an action of changing an image pickup magnification of the image pickup unit 1 is disposed at the operation portion 103. Note that the variable-power operation portion 107 may take any other form, such as a rotary switch, a push switch, or a touch sensor.

An endoscope connector 105 which is connected to an outside apparatus 120 is provided at a proximal end portion of the universal cord 104. The endoscope 101 also includes an electrical cable 115 and an optical fiber bundle 114 (not shown in FIG. 1) which are inserted so as to extend through the universal cord 104, the operation portion 103, and the insertion portion 102.

The electrical cable 115 is configured to electrically connect the connector portion 105 and the image pickup unit 1. The image pickup unit 1 is electrically connected to the outside apparatus 120 via the electrical cable 115 when the connector portion 105 is connected to the outside apparatus 120. Via the electrical cable 115, supply of power from the outside apparatus 120 to the image pickup unit 1 and communication between the outside apparatus 120 and the image pickup unit 1 are performed.

The optical fiber bundle 114 is configured to propagate light, which is given off from a light source portion of the outside apparatus 120, to the illuminating light emitting portion 113 of the distal end portion 110. Note that the light source portion may be disposed at the operation portion 103 or the distal end portion 110 of the endoscope 101.

The outside apparatus 120 is configured to include, for example, the light source portion, a power source portion 120a, an image processing unit 120b, and an image display portion 121. The power source portion 120a is configured to output power that causes the drive mechanism portion 30 of the image pickup unit 1 to act in response to a user's operation of the variable-power operation portion 107. As will be described in detail later, by way of example, the power source portion 120a is configured to apply current to a shape memory alloy wire (hereinafter abbreviated as an SMA wire) 41 which is a wire-like piece of shape memory alloy of the drive mechanism portion 30 in the present embodiment.

The image processing unit 120b is configured to generate a video signal on the basis of an image pickup device output signal outputted from the image pickup unit 1 and output the video signal to the image display portion 121. That is, an optical image picked up by the image pickup unit 1 is displayed as video on the image display portion 121. Note that some or all of the power source portion 120a, the image processing unit 120b, and the image display portion 121 may be disposed not at the outside apparatus 120 but at the endoscope 101.

Figure 2:
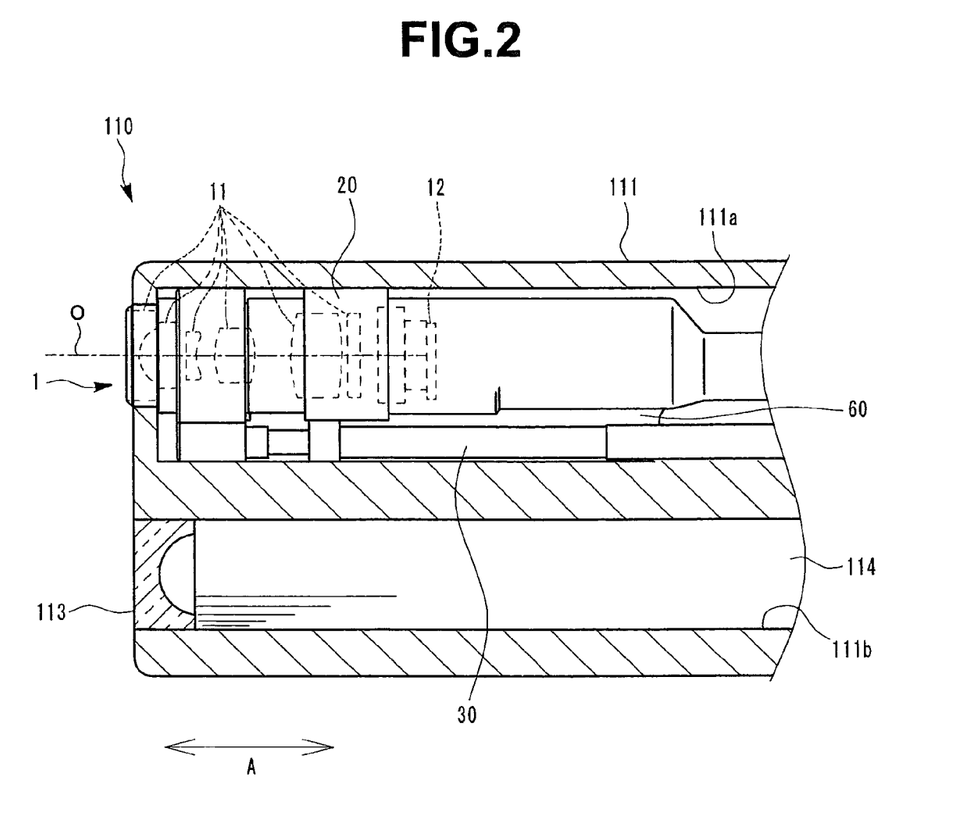
FIG. 2 is a cross-sectional view for explaining an outline of a distal end portion of an insertion portion in the endoscope.

A configuration of the distal end portion 110 will be described. As shown in FIG. 2, the image pickup unit 1 and the illuminating light emitting portion 113 are disposed at the distal end portion 110.

By way of example, in the present embodiment, the image pickup unit 1 is disposed along a longitudinal direction (an insertion axis direction) of the insertion portion 102 which is indicated by an arrow A in FIG. 2 so as to perform image pickup in a direction toward the distal end. More specifically, the image pickup unit 1 is disposed such that an optical axis O of objective lenses 11 is along the longitudinal direction of the insertion portion 102. Note that the image pickup unit 1 may be disposed such that the optical axis O forms a predetermined angle with the longitudinal direction of the insertion portion 102.

The illuminating light emitting portion 113 is configured to emit light which is emitted from a distal end of the optical fiber bundle 114 such that an object for the image pickup unit 1 is illuminated with the light. In the present embodiment, the illuminating light emitting portion 113 is configured to emit light in the direction toward the distal end from a distal end face of the distal end portion 110 along the longitudinal direction of the insertion portion 102.

The image pickup unit 1 and the illuminating light emitting portion 113 are held by a holding portion 111 which is provided at the distal end portion 110. The holding portion 111 is a rigid member which is exposed at the distal end face of the distal end portion 110 and is provided with through-holes 111a and 111b which are pierced along the longitudinal direction of the insertion portion 102. Inside the through-holes 111a and 111b, the image pickup unit 1 and the illuminating light emitting portion 113 are fixed by a method, such as adhesive or screwing. The optical fiber bundle 114 is inserted from a proximal end side and is fixed inside the through-hole 111b.

Figure 3:
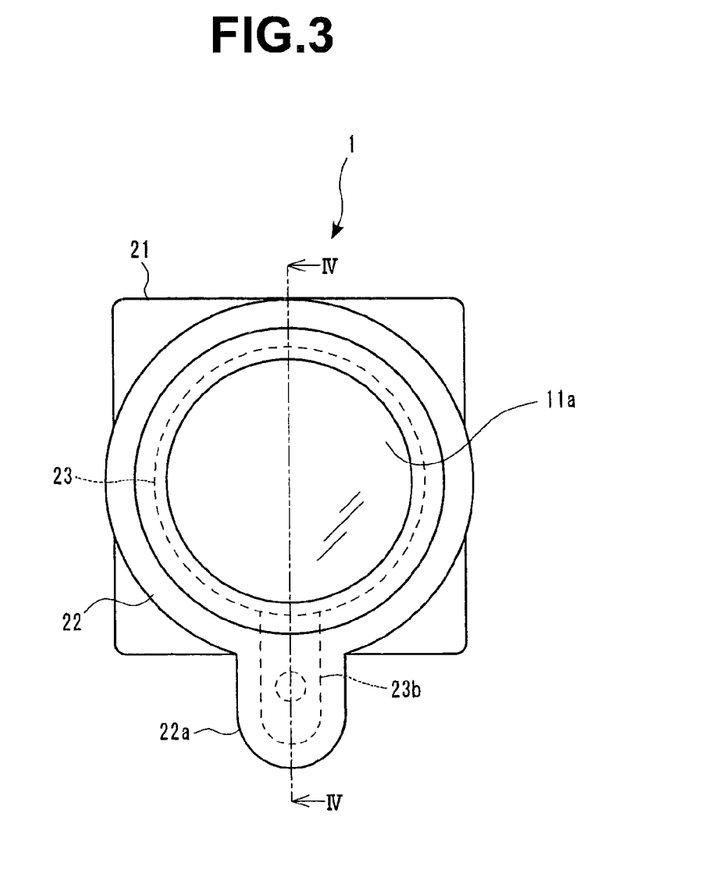
FIG. 3 is a front view of the image pickup unit for an endoscope, as seen from a distal end side.

A configuration of the image pickup unit 1 according to the present embodiment will be described. As shown in FIGS. 2 and 3, the image pickup unit 1 is configured to include a lens barrel portion 20 which holds the objective lenses 11 and an image pickup device 11 disposed closer to an image side than the objective lenses 11 and the drive mechanism portion 30 that is disposed at a side portion of the lens barrel portion 20.

Figure 4:
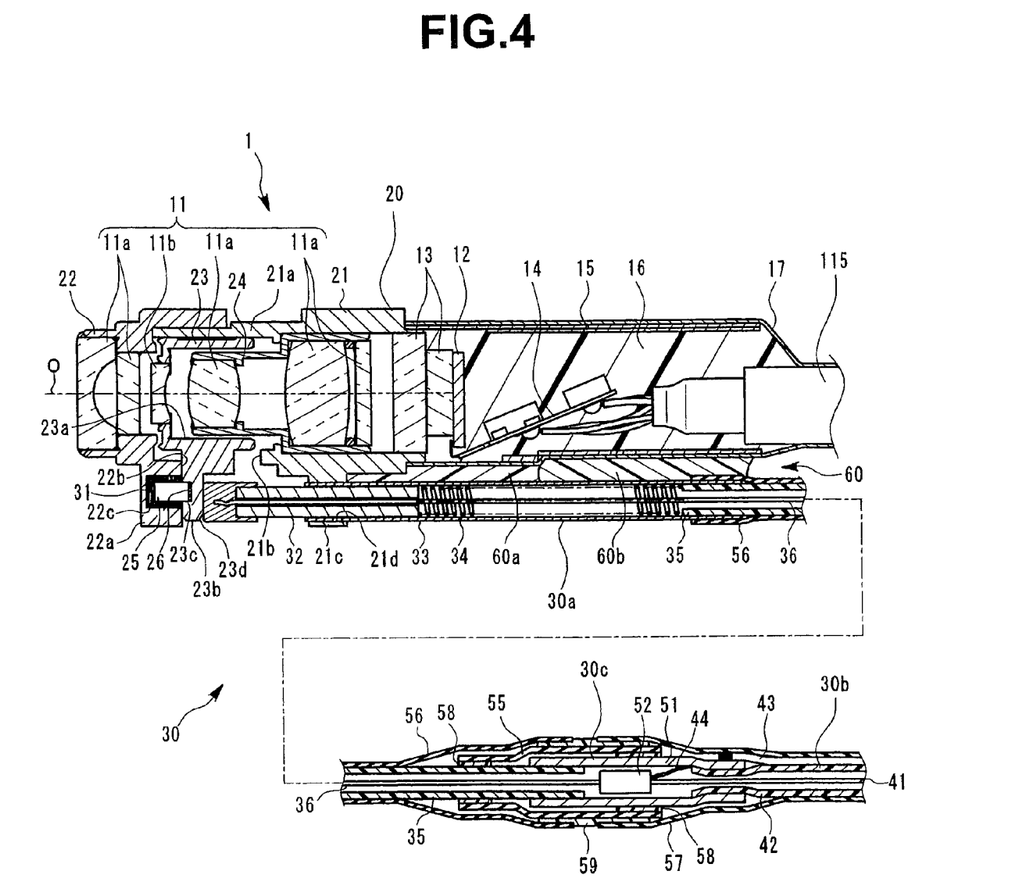
FIG. 4 is a cross-sectional view taken along line IV-IV in FIG. 3.

As shown in a cross-sectional view in FIG. 4, the objective lenses 11 are composed of a plurality of optical system members, such as lenses, which form an object image. The objective lenses 11 according to the present embodiment are configured to include a fixed lens 11a which is composed of one or a plurality of lenses with fixed positions inside the lens barrel portion 20 and a movable lens 11b which is composed of one or a plurality of lenses movable in a direction of the optical axis O inside the lens barrel portion 20. By way of example, in the present embodiment, the objective lenses 11 are configured such that the photographing magnification increases (an angle of view decreases) with increase in proximity of the movable lens 11b to the image side.

Note that although the objective lenses 11 according to the present embodiment are formed such that the photographing magnification increases with increase in the proximity of the movable lens 11b to the image side, the objective lenses 11 may be formed such that the photographing magnification decreases with increase in the proximity of the movable lens 11b to the image side. In the present embodiment, the fixed lenses 11a are disposed in front of and behind the movable lens 11b. The movable lens 11b may, however, be disposed closest to an object side among the objective lenses 11 or be disposed closest to the image side among the objective lenses 11. The objective lenses 11 may be configured to include any other optical system member, such as a diaphragm, a prism, or an optical filter.

The image pickup device 12 has a plurality of light-receiving elements in an array which photoelectrically convert incident light. For example, an image pickup device referred to as, e.g., a CCD (charge coupled device) or a CMOS (complementary metal oxide semiconductor) sensor or any of various other image pickup devices can be generally used as the image pickup device 12. The image pickup device 12 is disposed such that the light-receiving devices are located at an image formation surface of the objective lenses 11.

Cover glasses 13 are glued with adhesive to a light-receiving surface, at which the light-receiving devices are disposed, of the image pickup device 12. A circuit substrate 14 is electrically connected to the image pickup device 12. The circuit substrate 14 is electrically connected to the electrical cable 115.

A configuration of the lens barrel portion 20 will first be described. The lens barrel portion 20 that holds the objective lenses 11 and the image pickup device 12 described above is configured to include a fixed barrel 21, an object-side lens holding barrel 22, a movable lens holding barrel 23, and an image-side lens holding barrel 24. The fixed barrel 21, the object-side lens holding barrel 22, and the image-side lens holding barrel 24 are members with quasi-cylindrical shapes, respectively, and positions of the components are fixed by, e.g., adhesive or press fitting.

The cover glasses 13 are fixed with adhesive to a proximal end side of the fixed barrel 21. That is, the image pickup device 12 is fixed to the proximal end side of the fixed barrel 21 via the cover glasses 13.

A circular cylindrical portion 21a with a quasi-circular cylindrical shape is provided on a distal end side of the fixed barrel 21. A slit 21b that is a through-hole in which an arm portion 23b of the movable lens holding barrel 23 (to be described later) is inserted so as to extend through the through-hole is formed in a side surface portion of the circular cylindrical portion 21a. The slit 21b is a long hole, a longitudinal direction of which is substantially parallel to the optical axis O.

A holding portion 21c which protrudes outwardly in a radial direction (a direction orthogonal to the optical axis O) in an arm-like manner is provided closer to the proximal end side than the slit 21b on a side surface of the fixed barrel 21. The slit 21b and the holding portion 21c are provided in substantially same circumferential directions relative to the optical axis O, as seen from the direction of the optical axis O. As will be described in detail later, the holding portion 21c is a part which positions and holds a distal end portion of a guide pipe 33 constituting the drive mechanism portion 30. More specifically, a through-hole 21d which is substantially parallel to the optical axis O is formed in the holding portion 21c, and the substantially circular cylindrical guide pipe 33 is fixed while being inserted so as to extend through the through-hole 21d. As will be described in detail later, a pressing portion 32 is disposed inside the guide pipe 33 so as to be movable to advance and retract in the direction of the optical axis O.

The object-side lens holding barrel 22 is fixed on a distal end side of the circular cylindrical portion 21a of the fixed barrel 21. The object-side lens holding barrel 22 is a substantially circular cylindrical member which holds the fixed lens 11a that is located closer to the object side than the movable lens 11b among the objective lenses 11.

A restraining convex portion 22a which protrudes outward in the radial direction (the direction orthogonal to the optical axis O) in an arm-like manner is provided at a side surface of the object-side lens holding barrel 22. The restraining convex portion 22a is provided in a substantially same circumferential direction as the circumferential direction for the slit 21b to the optical axis O, as seen from the direction of the optical axis O. As will be described in detail later, the restraining convex portion 22a is a part constituting a portion of the drive mechanism portion 30. A flat portion 22b which is substantially orthogonal to the optical axis O is formed on a proximal end side of the restraining convex portion 22a. A substantially circular concave portion 22c which is provided to be recessed in the direction of the optical axis O is formed in the flat portion 22b. The concave portion 22c is disposed such that a center position of the concave portion 22c deviates from a center position of the through-hole 21d that is provided in the holding portion 21c of the fixed barrel 21, as seen from the direction of the optical axis O. More specifically, the concave portion 22c is disposed inside the through-hole 21d of the fixed barrel 21 in the radial direction, as seen from the direction of the optical axis O.

Figure 5:
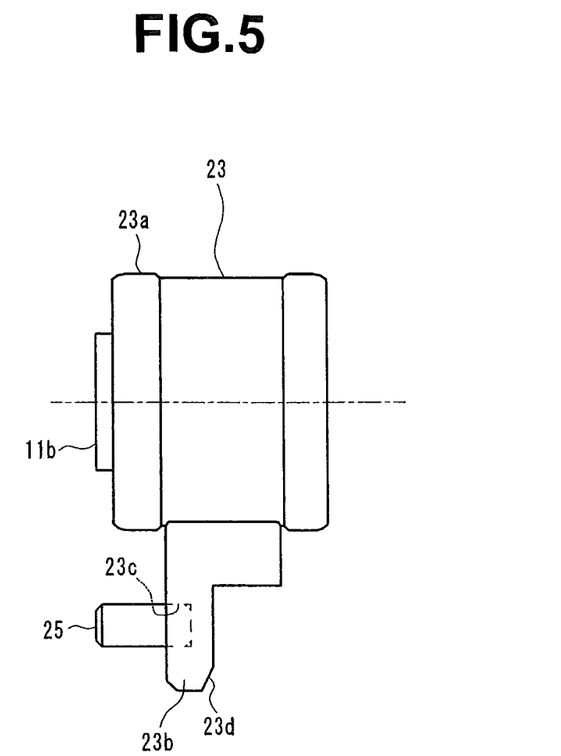
FIG. 5 is a side view of a movable lens holding barrel.

Inside the circular cylindrical portion 21a of the fixed barrel 21, the movable lens holding barrel 23 is disposed so as to be movable to advance and retract in the direction of the optical axis O. The movable lens holding barrel 23 is a member which holds the movable lens 11b among the objective lenses 11. As shown in FIG. 5, the movable lens holding barrel 23 is configured to have a substantially circular cylindrical lens holding portion 23a and an arm portion 23b which protrudes outward from a side surface of the lens holding portion 23a in the radial direction (the direction orthogonal to the optical axis O) in an arm-like manner.

The lens holding portion 23a is capable of holding the movable lens 11b inside. The lens holding portion 23a has an outer diameter which is set such that the lens holding portion 23a fits in the circular cylindrical portion 21a of the fixed barrel 21 with a predetermined gap with the circular cylindrical portion 21a and is configured to be slidable in the direction of the optical axis O inside the circular cylindrical portion 21a. In a state in which the lens holding portion 23a fits in the circular cylindrical portion 21a, the arm portion 23b is inserted so as to extend through the slit 21b. Rotation of the movable lens holding barrel 23 about the optical axis O is regulated by the arm portion 23b inserted so as to extend through the slit 21b.

In the state in which the lens holding portion 23a fits in the circular cylindrical portion 21a, the arm portion 23b protrudes outward from the circular cylindrical portion 21a in the radial direction. More specifically, the arm portion 23b has a length enough to protrude outward in the radial direction to a position which overlaps with a center of the through-hole 21d that is provided in the holding portion 21c of the fixed barrel 21.

Figure 6:
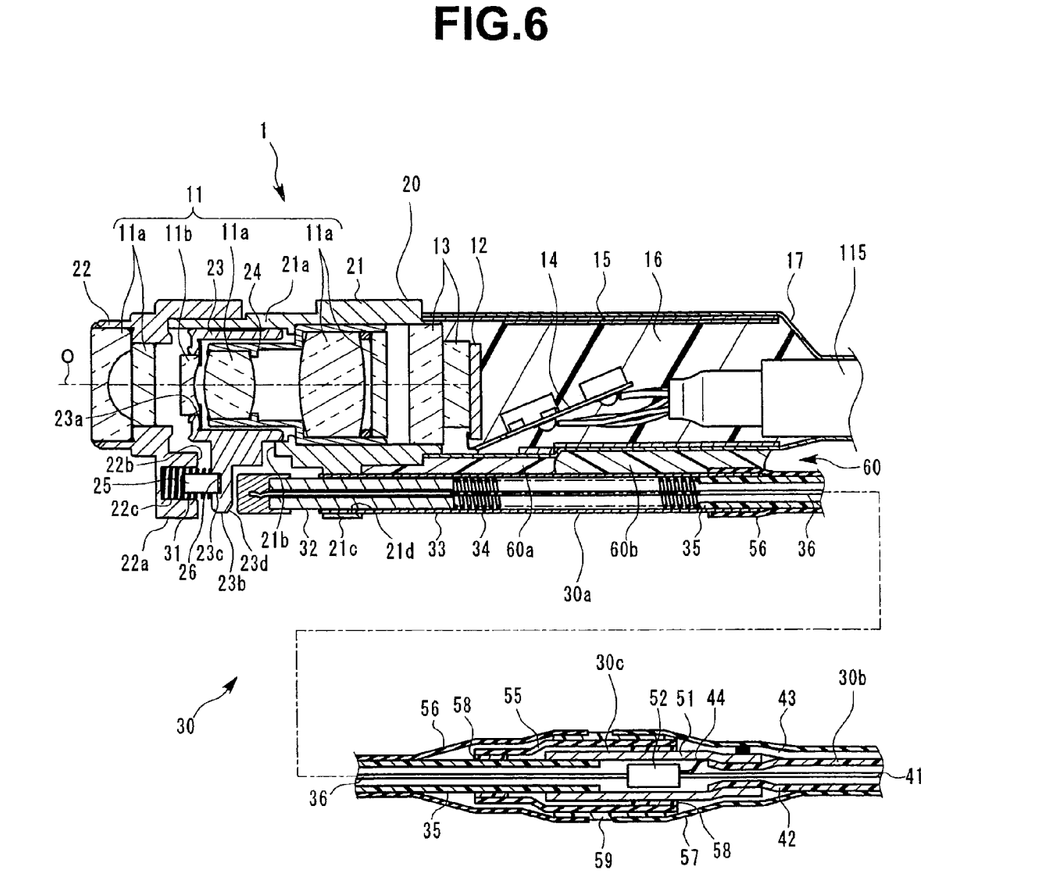
FIG. 6 is a view showing a state in which the movable lens holding barrel has been moved toward a proximal end side in a cross-section in FIG. 4.

The arm portion 23b is provided so as to abut on the flat portion 22b of the restraining convex portion 22a in the object-side lens holding barrel 22 before the lens holding portion 23a abuts when the movable lens holding barrel 23 is moved to a distal end side (the object side). FIG. 4 shows a state in which the arm portion 23b abuts on the flat portion 22b of the restraining convex portion 22a, and the movable lens holding barrel 23 is located closest to the distal end side within a movable range. The arm portion 23b is provided so as to abut on a part (not shown) of the fixed barrel 21 or a spacer (not shown) fixed to the fixed barrel 21 before the lens holding portion 23a abuts when the movable lens holding barrel 23 is moved to a proximal end side (the image side). FIG. 6 shows a state in which the arm portion 23b abuts on the fixed barrel 21 or the spacer, and the movable lens holding barrel 23 is located closest to the proximal end side within the movable range. As described above, in the present embodiment, the movable range in the direction of the optical axis O of the movable lens holding barrel 23 is defined to extend to a point where the arm portion 23b abuts on the fixed part of the fixed barrel 21.

The movable lens holding barrel 23 moves in the direction toward the distal end when the arm portion 23b is pressed by the pressing portion 32 (to be described later). The pressing portion 32 is disposed along the guide pipe 33 that is inserted so as to extend through the through-hole 21d of the holding portion 21c so as to be movable to advance and retract in the direction of the optical axis O. If the center positions of the concave portion 22c and the through-hole 21d substantially coincide with each other, as seen from the direction of the optical axis O, when the movable lens holding barrel 23 is located at a most distal end of the movable range, the arm portion 23b may enter the concave portion 22c, and the movable lens holding barrel 23 may be tilted. The tilt of the movable lens holding barrel 23 may cause deviation in field of view or focus deviation. For the reason, in the present embodiment, an area over which the flat portion 22b and the arm portion 23b abut on each other is widened by deviating the center positions of the concave portion 22c and the through-hole 21d from each other, as described above. With the configuration, the movable lens holding barrel 23 is prevented from being tilted.

A chamfered sloping portion 23d is formed at a corner on a proximal end side at an outer end portion in the radial direction of the arm portion 23b. The proximal end side of the arm portion 23b is a part which is urged toward the distal end side by the pressing portion 32 (to be described later). The press on the arm portion 23b separate from the optical axis O causes torque to be imparted to the movable lens holding barrel 23. If the torque is high, so-called "twisting" meaning that the movable lens holding barrel 23 is tilted inside the fixed barrel 21 may occur to cause the movable lens holding barrel 23 to fail at sliding. For the reason, in the present embodiment, a barycenter of a contact surface of the arm portion 23b and the pressing portion 32 is brought close to the optical axis O by providing the sloping portion 23d such that the torque to be imparted to the movable lens holding barrel 23 is low.

A concave portion 23c is provided in a surface on a distal end side of the arm portion 23b. A columnar core bar 25 is fitted in the concave portion 23c so as to protrude in a direction substantially parallel to the optical axis O. The core bar 25 is fixed with an adhesive 26 which is provided at a bottom portion of the concave portion 23c to the arm portion 23c. The core bar 25 is provided at a position where the core bar 25 protrudes into the concave portion 22c provided in the restraining convex portion 22a of the object-side lens holding barrel 22. The core bar 25 is a part for preventing buckling of a first spring 31 constituting the drive mechanism portion 30 (to be described later).

A film made of lubricant is formed in a region of the outer circumferential face, where an outer circumferential face of the movable lens holding barrel 23 is in contact with other members. By way of example, in the present embodiment, a fluorine coating agent is applied to an outer circumferential face in contact with the fixed barrel 21 of the lens holding portion 23a of the movable lens holding barrel 23. The application of the fluorine coating agent to the outer circumferential face of the movable lens holding barrel 23 allows the movable lens holding barrel 23 to smoothly move to advance and retract in the direction of the optical axis O.

Inside the circular cylindrical portion 21a of the fixed barrel 21, the image-side lens holding barrel 24 is fixed closer to the proximal end side than the movable lens holding barrel 23 and closer to the object side than the cover glasses 12. The image-side lens holding barrel 24 is a substantially circular cylindrical member which holds the fixed lens 11a that is located closer to the image side than the movable lens 11b among the objective lenses 11.

In a region closer to the proximal end side than the fixed barrel 21, the image pickup device 12, the circuit substrate 14, and a distal end portion of the electrical cable 115 are surrounded by a cylindrical shielding frame 15 which is made of a metallic thin plate, and the shielding frame 15 is filled with an electrically insulating sealing resin. The shielding frame 15 and the distal end portion of the electrical cable 115 are sheathed with a heat-shrinkable tube 17.

The movable lens holding barrel 23 described above of the lens barrel portion 20 is driven to advance and retract in the direction of the optical axis O by the drive mechanism portion 30 disposed at the side portion of the lens barrel portion 20.

A configuration of the drive mechanism portion 30 is not particularly limited as long as the drive mechanism portion 30 is disposed at the side portion of the lens barrel portion 20 and can drive the movable lens holding barrel 23 in the direction of the optical axis O. For example, the drive mechanism portion 30 may be a mechanism in which a distal end portion of a wire routed along the electrical cable 115 is fixed to the arm portion 23b and which drives the movable lens holding barrel 23 by pushing and pulling the wire by the lever provided at the operation portion 103 of the endoscope 101. Alternatively, for example, the drive mechanism portion 30 may be configured to drive the movable lens holding barrel 23 by a linear motor.

By way of example, in the present embodiment, the drive mechanism portion 30 is configured to drive the movable lens holding barrel 23 in the direction of the optical axis O through expansion and contraction of an SMA wire 41. The configuration of the drive mechanism portion 30 according to the present embodiment will be described below.

The drive mechanism portion 30 is configured to have a drive force transmitting portion 30a which is disposed at the side portion of the lens barrel portion 20, a drive force generating portion 30b which is disposed closer to the proximal end side than the drive force transmitting portion 30a, and a coupling portion 30c which connects the drive force transmitting portion 30a and the drive force generating portion 30b.

The drive mechanism portion 30 is configured to include the restraining convex portion 22a, the first spring 31, the pressing portion 32, the guide pipe 33, a second spring 34, a first outer tube 35, and an inner wire 36.

The guide pipe 33 is a circular cylindrical pipe and is fixed to the holding portion 21c while the distal end portion is inserted so as to extend through the through-hole 21d provided in the holding portion 21c of the fixed barrel 21. The guide pipe 33 is positioned and fixed at a side portion of the fixed barrel 21 by the holding portion 21c such that a central axis is substantially parallel to the optical axis O.

The first outer tube 35 is connected to a proximal end of the guide pipe 33. The first outer tube 35 is a pipe which is made of a synthetic resin, such as polyether ether ketone resin (PEEK). The inner wire 36 is inserted so as to extend through the first outer tube 35. The first outer tube 35 is configured to be bendable according to a manner in which the bending portion 109 of the insertion portion 102 in the endoscope 101 bends and resist tension added to the inner wire 36 inserted so as to extend through the first outer tube 35.

Inside the guide pipe 33, the piston-like pressing portion 32 is disposed to be freely slidable in an axial direction. The pressing portion 32 protrudes from a distal end of the guide pipe 33 in the direction toward the distal end and abuts on the arm portion 23b of the movable lens holding barrel 23. A distal end of the inner wire 36 is fixed to the pressing portion 32.

The second spring 34 that urges the pressing portion 32 in the direction toward the distal end is disposed inside the guide pipe 33. In the present embodiment, the second spring 34 is a compression coil spring. Thus, if tension is not added to the inner wire 36, the pressing portion 32 presses the arm portion 23b of the movable lens holding barrel 23 in the direction toward the distal end by urging force of the second spring 34.

The first spring 31 is disposed so as to urge the movable lens holding barrel 23 in a direction toward the proximal end. In the present embodiment, the first spring 31 is a compression coil spring and is disposed in the concave portion 22c provided in the restraining convex portion 22a of the object-side lens holding barrel 22. The first spring 31 is thus disposed across the arm portion 23b of the movable lens holding barrel 23 from the pressing portion 32.

The first spring 31 is configured here such that force urging the arm portion 23b in the direction toward the proximal end is weaker than force urging the arm portion 23b in the direction toward the distal end of the second spring 34. Thus, if tension is not added to the inner wire 36, the arm portion 23b moves in the direction toward the distal end by the urging force of the second spring 34 to abut on the restraining convex portion 22a, as shown in FIG. 4. That is, if tension is not added to the inner wire 36, the movable lens holding barrel 23 is located at a distal end of the movable range.

If tension is added to the inner wire 36, the second spring 34 contracts, and the pressing portion 32 moves in the direction toward the proximal end, the arm portion 23b moves toward the proximal end side by urging force of the first spring 31, as shown in FIG. 6. That is, the drive force transmitting portion 30a is configured such that the pressing portion 32 moves to advance and retract in the direction of the optical axis O in response to change in the tension of the inner wire 36 and is configured to move the movable lens holding barrel 23 in the direction of the optical axis O by the urging force of the first spring 31.

The drive force generating portion 30b is configured to produce tension to be added to the inner wire 36. The drive force generating portion 30b is configured to include the SMA wire 41, a second outer tube 42, an electric wire 43, and a lead wire 44. By way of example, in the present embodiment, the drive force generating portion 30b is provided so as to be located closer to the proximal end side than the bending portion 109 of the insertion portion 102 in the endoscope 101.

The second outer tube 42 is a pipe which is made of a synthetic resin, such as polyether ether ketone resin (PEEK), and the SMA wire 41 is inserted so as to extend through the second outer tube 42. The second outer tube 42 is configured to be bendable according to a manner in which the flexible tube portion 108 of the insertion portion 102 in the endoscope 101 bends and resist tension produced by the SMA wire 41 inserted so as to extend through the second outer tube 42.

A distal end of the second outer tube 42 is connected to a proximal end of the first outer tube 35 via a coupling pipe 51 of the coupling portion 30c. The coupling pipe 51 is a metallic tube. The proximal end of the first outer tube 35 and a distal end of the coupling pipe 51 are fixed with adhesive. A proximal end of the coupling pipe 51 and a proximal end of the second outer tube 42 are fixed through so-called swaging that presses hard on the coupling pipe 51.

The SMA wire 41 is configured to contract when temperature rises. A distal end of the SMA wire 41 is connected to a proximal end of the inner wire 36 inside the coupling pipe 51. The distal end of the SMA wire 41 and the proximal end of the inner wire 36 are connected by, for example, fixation through swaging that presses hard on the wire coupling portion 52 while both the ends are inserted so as to extend through the metallic tubular wire coupling portion 52.

A distal end of the electric wire 43 is electrically connected to a distal end portion of the SMA wire 41. More specifically, the distal end of the electric wire 43 is fixed to the coupling pipe 51 through soldering, and the electric wire 43 and the coupling pipe 51 are electrically connected. Inside the coupling pipe 51, the lead wire 44 for electrically connecting the coupling pipe 51 and the SMA wire 41 is disposed. The lead wire 44 has one end fixed to the coupling pipe 51 through soldering and the other end fixed to the distal end portion of the SMA wire 41 through soldering. The lead wire 44 is disposed with some slack so as to be capable of following motion of the distal end portion of the SMA wire 41 that moves to advance and retract in an axial direction inside the coupling pipe 51.

The electric wire 43 has a proximal end provided at the endoscope connector 105 and is configured so as to be electrically connectable to the power source portion 120a via the endoscope connector 105.

Although not shown, a proximal end of the SMA wire 41 is fixed to a proximal end of the second outer tube 42 such that a position in the longitudinal direction is not changed. A distal end of an electric wire (not shown) is electrically connected to a proximal end portion of the SMA wire 41. The electric wire electrically connected to the proximal end portion of the SMA wire 41 has a proximal end provided at the endoscope connector 105 and is configured so as to be electrically connectable to the power source portion 120a via the endoscope connector 105.

In the present embodiment, the SMA wire 41 is configured so as to be electrically connectable to the power source portion 120a via the one pair of electric wires, and current outputted from the power source portion 120a is applied to the SMA wire 41.

The SMA wire 41 generates heat corresponding to applied current and contracts according to the generated heat. The contraction of the SMA wire 41 causes tension to be added to the inner wire 36 connected to the distal end of the SMA wire 41. As described above, the drive force generating portion 30b is configured to generate driving force that drives the movable lens holding barrel 23.

A configuration of the drive mechanism portion 30 which maintains watertightness of the coupling portion 30c will be described. As shown in FIG. 4, in the coupling portion 30c, an outer circumference of a connection portion of the proximal end of the first outer tube 35 and the distal end of the coupling pipe 51 is sheathed with a first heat-shrinkable tube 55. A space between an inner circumferential face of a distal end portion of the first heat-shrinkable tube 55 and an outer circumferential face of the first outer tube 35 and a space between an inner circumferential face of a proximal end portion of the first heat-shrinkable tube 55 and an outer circumferential face of the coupling pipe 51 are filled with an adhesive 58. With the configuration, watertightness at the connection portion of the proximal end of the first outer tube 35 and the distal end of the coupling pipe 51 is realized.

A portion from the outer circumferential face of the first outer tube 35 to an outer circumferential face of the first heat-shrinkable tube 55 is sheathed with a second heat-shrinkable tube 56. A proximal end portion of the second heat-shrinkable tube 56 is fixed with an adhesive 59 with which a space between the proximal end portion and the outer circumferential face of the first heat-shrinkable tube 55 is filled.

A portion from the outer circumferential face of the first heat-shrinkable tube 55 to an outer circumferential face of the second outer tube 42 in a region closer to the proximal end side than the second heat-shrinkable tube 56 is sheathed with a third heat-shrinkable tube 57. A distal end portion of the third heat-shrinkable tube 57 is fixed with the adhesive 59, with which a space between the distal end portion and the outer circumferential face of the first heat-shrinkable tube 55 is filled.

As described above, a heat-shrinkable tube with which the drive mechanism portion 30 is sheathed in order to maintain watertightness in the drive mechanism portion 30 according to the present embodiment is divided at the coupling portion 30c into two, the second heat-shrinkable tube 56 and the third heat-shrinkable tube 57.

A heat-shrinkable tube, with which a part inserted so as to extend through the bending portion 109 of the drive mechanism portion 30 is sheathed, is large in the amount of deformation and is relatively susceptible to damage. For example, in the case of a conventional configuration in which a whole of a drive mechanism portion is sheathed with one heat-shrinkable tube, watertightness in the drive mechanism portion cannot be maintained if a hole is formed in the heat-shrinkable tube. In contrast, in the present embodiment, even if a hole is formed in, for example, the second heat-shrinkable tube 56, watertightness in the coupling portion 30c is ensured by the first heat-shrinkable tube 55 and the third heat-shrinkable tube 57.

Since a portion where the proximal end of the coupling pipe 51 and the proximal end of the second outer tube 42 are fixed is a portion which is fixed through swaging, moisture is likely to enter the coupling portion 30c through the portion. The part, through which moisture is likely to enter the coupling portion 30c, is sheathed with the third heat-shrinkable tube 57 that is not disposed inside the bending portion 109 and is insusceptible to damage, and watertightness in the coupling portion 30c can thus be reliably maintained.

As has been described above, the image pickup unit 1 according to the present embodiment is configured to include the lens barrel portion 20 and the drive mechanism portion 30 disposed at the side portion of the lens barrel portion 20. In the present embodiment, a gap is formed between the lens barrel portion 20 and the drive mechanism portion 30.

More specifically, a portion closer to the proximal end side than the holding portion 21c of the drive mechanism portion 30 has a quasi-circular cylindrical shape extending toward the proximal end side in the direction of the optical axis O. An outer diameter of the portion with the circular cylindrical shape extending toward the proximal end side of the drive mechanism portion 30 is substantially same to the coupling portion 30c, though the outer diameter becomes somewhat large due to presence of the second heat-shrinkable tube 56. The shielding frame 15 closer to the proximal end side than the holding portion 21c of the lens barrel portion 20 becomes smaller in diameter toward the proximal end side in order to avoid interference with components incorporated in the bending portion 109 and the flexible tube portion 108. The tendency becomes more remarkable due to reduction in size of the image pickup device 12 and the circuit substrate 14.

For the reason, a gap forms between the shielding frame 15 that becomes smaller in diameter toward the proximal end side and the drive mechanism portion 30 that extends linearly with a substantially same outer diameter toward the proximal end side. More specifically, the gap formed between the shielding frame 15 and the drive mechanism portion 30 becomes wider toward the proximal end side.

In the image pickup unit 1 according to the present embodiment, the gap formed between the shielding frame 15 and the drive mechanism portion 30 is filled with an adhesive 60. The adhesive 60 is made to have a difference in hardness after curing between a distal end side and a proximal end side and is configured such that hardness on the proximal end side is lower than hardness on the distal end side.

A configuration for making the hardness of the adhesive 60 lower on the proximal end side than on the distal end side is not particularly limited. By way of example, in the present embodiment, the gap is filled on the distal end side with a high-hardness adhesive 60a which is relatively high in hardness after curing and is filled on the proximal end side with a low-hardness adhesive 60b which is lower in hardness after curing than the high-hardness adhesive 60a. Note that the number of types of adhesives different in hardness is not limited to two. The number may be three or more.

In other words, in the present embodiment, the gap formed between the shielding frame 15 and the drive mechanism portion 30 is filled with the adhesive 60, the hardness of which increases with increase in proximity to a root of the drive mechanism portion 30 that extends from a side surface portion of the lens barrel portion 20 to fix the lens barrel portion 20 and the drive mechanism portion 30.

According to the image pickup unit 1 described above of the present embodiment, the drive mechanism portion 30 can be firmly fixed to the lens barrel portion 20 at a predetermined position without misregistration by filling a portion of the gap which is close to the root of the drive mechanism portion 30 extending from the side surface portion of the lens barrel portion 20 with the high-hardness adhesive 60a.

Figure 7:
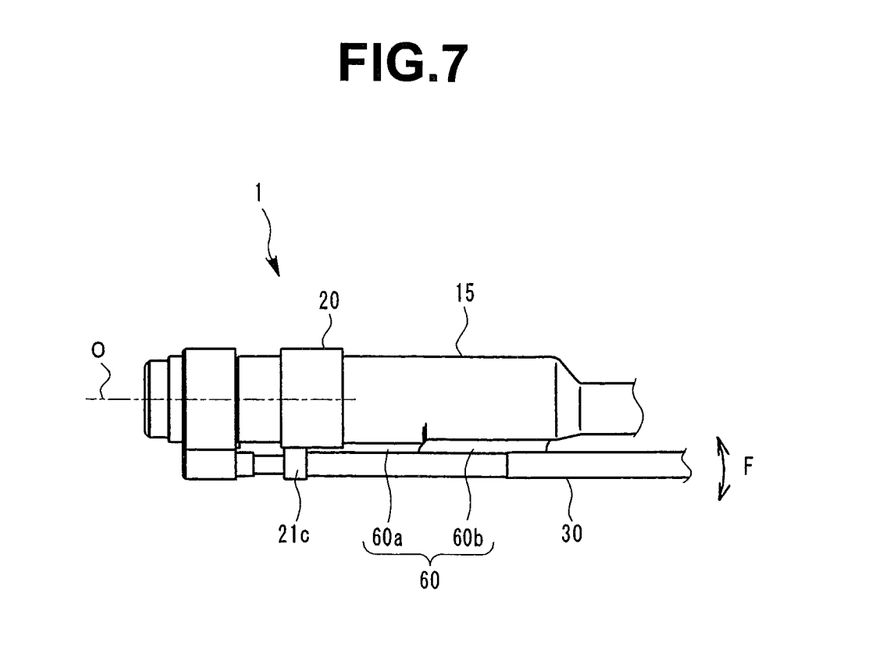
FIG. 7 is a view for explaining effects of an adhesive.

If a force for moving a proximal end side of the drive mechanism portion 30 is added to the lens barrel portion 20, as indicated by an arrow F in FIG. 7, the low-hardness adhesive 60b, with which the proximal end side of the gap is filled and which is low in hardness and is relatively flexible, is deformed to follow movement of the proximal end side of the drive mechanism portion 30 without exfoliating. The deformation of the low-hardness adhesive 60b alleviates a force added to the high-hardness adhesive 60a through the movement of the proximal end side of the drive mechanism portion 30.

For example, if work of inserting the image pickup unit 1 into the through-hole 111a in the holding portion 111 is performed at the time of assembly of the endoscope 101, a worker grasping the image pickup unit 1 may cause a force which moves the proximal end side of the drive mechanism portion 30 relative to the lens barrel portion 20, as indicated by the arrow F in FIG. 7, to be added to the image pickup unit 1. However, according to the present embodiment, since the force is alleviated through deformation of the low-hardness adhesive 60b, and the portion where the shielding frame 15 and the drive mechanism portion 30 are fixed is firmly fixed with the high-hardness adhesive 60a, exfoliation of the high-hardness adhesive 60a and breakage of an adhesive portion which fixes the holding portion 21c of the fixed barrel and the guide pipe 33 can be prevented.

In contrast to the present embodiment, for example, if the gap formed between the shielding frame 15 and the drive mechanism portion 30 is filled with an adhesive relatively high in hardness and uniform in hardness, when a force which moves the proximal end side of the drive mechanism portion 30 relative to the lens barrel portion 20 is added to the image pickup unit 1, the adhesive is not deformed and exfoliates from the proximal end side. For example, if the gap formed between the shielding frame 15 and the drive mechanism portion 30 is filled with an adhesive relatively low in hardness and uniform in hardness, when a force which moves the proximal end side of the drive mechanism portion 30 relative to the lens barrel portion 20 is added to the image pickup unit 1, a whole of the adhesive is deformed, and the drive mechanism portion 30 moves relative to the lens barrel portion 20. For the reason, the adhesive portion that fixes the holding portion 21c of the fixed barrel 21 and the guide pipe 33 may be broken or the holding portion 21c may be broken.

Since a high-hardness adhesive generally has low viscosity and high flowability before curing, it is relatively difficult to fill the high-hardness adhesive into a wide gap and cure the high-hardness adhesive. In the present embodiment, the gap is narrow at a spot where the high-hardness adhesive 60a is filled, and work can be easily performed.

Note that although a plurality of types of adhesives different in hardness is used in the above-described embodiment to decrease the hardness of the adhesive 60 to be filled into a gap formed between the lens barrel portion 20 and the drive mechanism portion 30 toward the proximal end side, the present invention is not limited to the configuration. For example, if the adhesive 60 is an adhesive having hardness after curing which varies according to cure temperature, the present invention can be realized by filling the gap with one type of adhesive and curing the adhesive with different cure temperatures for the distal end side and the proximal end side.

Note that the present invention is not limited to the above-described embodiment and can be appropriately changed without departing from the scope or spirit of the invention readable from the claims and the entire specification. An image pickup unit for an endoscope which involves such changes is also included in the technical scope of the present invention.

What is claimed is:

1. An image pickup unit for an endoscope, comprising:
   a lens barrel portion which is configured to hold an objective lens including a movable lens disposed on a distal end side and an image pickup device disposed closer to a proximal end side than the objective lens and includes a movable lens holding barrel that holds the movable lens and is movable to advance and retract; and
   a drive mechanism portion which is disposed at a side surface portion of the lens barrel portion and drives the movable lens holding barrel,
   wherein the unit has a holding portion which is disposed at the side surface portion of the lens barrel portion and is configured to position and hold the drive mechanism portion,
   the drive mechanism portion is shaped to extend in a direction toward a proximal end with a gap with the lens barrel portion on a side closer to the proximal end than the holding portion, and
   the gap between the lens barrel portion and the drive mechanism portion is filled with an adhesive which is made to have a difference in hardness such that hardness is lower on a proximal end side than on a distal end side.

2. The image pickup unit for an endoscope according to claim 1, wherein the adhesive made to have the difference in hardness comprises a plurality of adhesives different in hardness.

3. The image pickup unit for an endoscope according to claim 1, wherein the adhesive made to have the difference in hardness comprises a single type of adhesive which is made to vary in hardness.

* * * * *